United States Patent [19]

Weigel

[11] Patent Number: 5,428,176

[45] Date of Patent: Jun. 27, 1995

[54] PROCESS FOR PREPARING 2,2-DIFLUOROKETENE SILYL O,S-ACETALS AND α,α-DIFLUORO-β-SILYLOXY-1,3-DIOXOLANE-4-PROPANOIC ACID O,S-ESTERS

[75] Inventor: John A. Weigel, Lafayette, Ind.

[73] Assignee: Eli Lilly and Company, Indianapolis, Ind.

[21] Appl. No.: 227,820

[22] Filed: Apr. 14, 1994

[51] Int. Cl.⁶ .................... C07D 317/18; C07F 7/04
[52] U.S. Cl. ........................ 549/214; 549/4; 556/427; 556/429; 556/470
[58] Field of Search ............ 549/214, 4; 556/427, 556/429, 470

[56] References Cited

U.S. PATENT DOCUMENTS

| | | | |
|---|---|---|---|
| 4,414,372 | 11/1983 | Farnham et al. | 526/190 |
| 4,417,034 | 11/1983 | Webster | 526/190 |
| 4,482,729 | 11/1984 | Ishikawa et al. | 556/446 |
| 4,508,880 | 4/1985 | Webster | 526/190 |
| 4,526,988 | 7/1985 | Hertel | 549/313 |
| 4,746,750 | 5/1988 | Revis | 556/443 |
| 4,754,046 | 6/1988 | Revis | 556/401 |
| 4,824,980 | 4/1989 | Schulz, Jr. et al. | 556/413 |
| 4,824,981 | 4/1989 | Schulz, Jr. et al. | 556/443 |
| 5,041,587 | 8/1991 | Itoh et al. | 556/413 |

FOREIGN PATENT DOCUMENTS

| | | |
|---|---|---|
| 0184692 | 6/1986 | European Pat. Off. |
| 2067250 | 3/1990 | Japan . |
| 2270841 | 11/1990 | Japan . |

OTHER PUBLICATIONS

Ainsworth C., et al., *J. Organometallic Chem.*, 46 (1972), pp. 59–71.

Kita, Y., et al., *Tetrahedron Letters*, 24:12 (1983), pp. 1273–1276.

Brown, C., *J. Org. Chem.*, 39:9 (1974), pp. 1324–1325.

Kuo, Y., et al., *Chemical Communications*, (1971), pp. 136–137.

Petrov, A., et al., *J. Gen. Chem.*, (U.S.S.R.), 29 (1959) pp. 2896–2899.

Ojima, I., et al., *J. Organometallic Chem.*, 111(1976), pp. 43–60.

Howe, J., et al., *J. Organometallic Chem.*, 208 (1981), pp. 401–406.

Yoshii, E., et al., *Chem. Pharm. Bull.*, 22:11 (1974), pp. 2767–2769.

Ainsworth, C., and Chen, F., *J. Am. Chem. Soc.*, 94:11 (1972), pp. 4037–4038.

Kitagawa, O., et al., *Tetrahedron Letters*, 29:15 (1988), pp. 1803–1806.

Burton, D., and Eason, J., *J. of Fluorine Chemistry*, 38 (1988), pp. 125–129.

Kuroboshi, M., and Ishihara, T., *The Chemical Society of Japan*, 63 (1990), pp. 428–437.

Taguchi, T., et al., *Tetrahedron Letters*, 29:41 (1988), pp. 5291–5294.

Takeuchi, Y., et al., *J. Chem. Soc. Perkin Trans. I.* (1988), pp. 1149–1153.

Greuter, H., et al., *Tetrahedron Letters*, 29:27 (1988), pp. 3291–3294.

Yamana, M., et al., *Tetrahedron Letters*, 24:5 (1983), pp. 507–510.

Easdon, J., New Synthetic Methodology for Organofluorine Compounds, Thesis Jul. 1987, University of Iowa, pp. 162–206 and pp. 267–278.

Lang, R., and Schaub, B., *Tetrahedron Letters*, 29:24 (1988), pp. 2943–2946.

Mcharek, S., et al., *J. of Organometallic Chem.*, 401 (1991) pp. 211–215.

Lang, R., *Helvetica Chemica Acta*, 71 (1988), pp. 369–373.

Kitagawa, O., et al., *Chemistry Letters (Japan)*, pp. 1307–1310.

(List continued on next page.)

*Primary Examiner*—Cecilia Tsang
*Attorney, Agent, or Firm*—Robert A. Conrad; David E. Boone; Gerald V. Dahling

[57] ABSTRACT

Processes for preparing 2,2-difluoroketene silyl O,S-acetals and α,α-difluoro-β-silyloxy-1,3-dioxolane-4-propanoic acid O,S-esters.

13 Claims, No Drawings

OTHER PUBLICATIONS

Kobayashi, et al., Tetrahedron Letters, 29:15 (1988), pp. 1803–1806.

Tanaka, K., et al., Chemistry Letters, (1979), pp. 175–178.

Muzzard, M., et al., J. Org. Chem., 58 (1993), pp. 29–31.

Gimbert, Y., et al., Tetrahedron Letters, 32:37 (1991), pp. 4897–4900.

Purrington, S. and Sheu, K., Tetrahedron Letters, 33:23 (1992), pp. 3289–3292.

DeCock, Ch., et al., Tetrahedron Letters, 41:19 (1989), pp. 4183–4189

Piettre, S., et al., Tetrahedron Letters, 43:19 (1987), pp. 4309–4919.

Purrington S., et al., Jour. Fluorine Chem. 43 (1989), pp. 229–234.

Robert W. Lang et al., Tetrahedron Letters vol. 29, No. 24 pp. 2943–2946 (1988).

Hans Greuter et al., Tetrahedron Letters vol. 29, No. 27, pp. 3291–3294 (1988).

Kitagawa et al., Tetrahedron Letters vol. 29, No. 15, pp. 1803–1806 (1988).

PROCESS FOR PREPARING 2,2-DIFLUOROKETENE SILYL O,S-ACETALS AND α,α-DIFLUORO-β-SILYLOXY-1,3-DIOXOLANE-4-PROPANOIC ACID O,S-ESTERS

BACKGROUND OF THE INVENTION

1. Field of the Invention

The invention pertains to the field of pharmaceutical chemistry and provides a process for preparing 2,2-difluoroketene silyl O,S-acetal and α,α-difluoro-β-silyloxy-1,3-dioxolane-4-propanoic acid O,S-ester from same.

2. State of the Art

Ketene silyl acetals were first prepared by Petrov, et al.; see *J. Gen. Chem.* (USSR), 29, 2896–99 (1959). Almost thirty years later, H. Greuter, et al. in *Tetrahedron Lett.*, 29 (27), 3291–94 (1988) taught the use of allylic esters of chlorodifluoroacetic acid in silicon induced Reformatsky-Claisen reactions where 2,2-difluoroketene silyl acetals were inferred to be intermediates. Kobayashi, et al. in Japanese Patent 0,267,250 and *Tetrahedron Lett.*, 29 (15), 1803–06 (1988) described the preparation of 2,2-difluoro ketene silyl acetals by reacting methyl iododifluoro acetate with zinc dust in acetonitrile and treating of the resultant organozinc species (a Reformatsky reagent) with trialkylsilyl chloride. The authors also disclosed the preparation of 2,2-difluoro-2,2-dimethyl-β-(trialkylsilyl)oxy]-1,3-dioxolane-4-propanoic acid methyl esters by reacting 2,3-O-isopropylidene-D-gtyceraldehyde with difluoro ketene silyl acetals generated in situ. It was discovered that difluoro ketene silyl acetals afforded a much higher erythro/threo (anti/syn) ratio than Reformatsky reagents condensed with 2,3-O-isopropylidene glyceraldehydes. Matsumura, et al. in Japanese Patent 2,270,841, described the preparation of anti-α, α-difluoro-2,2-dimethyl-β-[(trialkylsilyl)oxy]-1,3-dioxolane-4-propanoic acid methyl esters which called for reacting methyl iododifluoro acetate with trialkyl silyl chloride and zinc, in acetonitrile, and treating the resulting mixture with 2,3-O-isopropylidene-D-glyceraldehyde and titanocene dichloride. J. C. Easdon in *New Synthetic Methodology for Organofluorine Compounds*, Ph.D. Thesis, Chemistry Department, Graduate College of the University of Iowa, July 1987, attempted to make 2,2-difluoroketene silyl acetals by reacting a difluoro acetate ester with lithium hexamethylsilazide and trimethylchlorosilane in tetrahydrofuran at −78° C. R. W. Lang, et al., *Tetrahedron Lett.*, 29 (24), 2943–6 (1988) reported that esters of chlorodifluoroacetic acid undergo Reformatsky-type condensation reactions with aldehydes if treated with activated zinc dust in dimethylformamide. However, lower yields were obtained when aliphatic, enolizable aldehydes, were condensed with chlorodifluoro acetate under similar conditions, unless ultrasonication was used. S. Mcharek, et al., *J. Organometallic Chem.*, 401, 211–15 (1991) reported Reformatsky-type condensation reactions requiring the use of methyl chlorodifluoroacetate and simple aliphatic aldehydes in dimethylformamide, or mixtures of methylene chloride and dimethylformamide, and electrolytic reduction (zinc anode and nickel catalyst). α,α-Difluoro-β-silyloxy-1,3-dioxolane-4-propanoic acid esters such as α,α-difluoro-2,2-dimethyl-β-[(trialkylsilyl)oxy]-1,3-dioxolane-4-propanoic acid methyl ester are used as intermediates in the preparation of antitumor and antiviral nucleoside agents; see for example U.S. Pat. No. 4,526,988.

An object of the present invention is to provide a process for preparing a 2,2-difluoroketene silyl O,S-acetals from chlorodifluoro thioacetates and difluoro thioacetates.

Another object of the present invention is to provide a process for preparing α,α-difluoro-β-silyloxy-1,3-dioxolane-4-propanoic acid O,S-esters from 2,2-difluoroketene silyl O,S-acetals.

Other objects and advantages of the present invention will become apparent from the following description and the embodiments contained therein.

SUMMARY OF THE INVENTION

The invention is a process for preparing a 2,2-difluoroketene silyl O,S-acetal of the formula

wherein $R^1$, $R^2$, $R^3$, and $R^4$ are independently selected from alkyl and aryl groups;

comprising contacting a difluoro O,S-acetate of the formula

wherein Z is chloro or hydrogen and $R^4$ is as defined above;

with a halosilane of the formula

wherein X is chloro or bromo and $R^1$, $R^2$, and $R^3$ are as defined above;

in a solvent;

provided that when said Z is chloro, the reaction is carried out in the presence of a reducing agent and the contact temperature ranges from about 25° C. to about 80° C.; further provided that when said Z is hydrogen, a base is added and the contact temperature ranges from about −78° C. to about 25° C.

In another aspect, the invention is a process for preparing a α,α-difluoro-β-silyloxy-1,3-dioxolane-4-propanoic acid thioesters of the formula

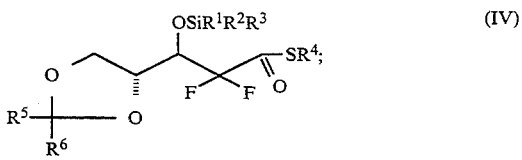

wherein $R^1$, $R^2$, $R^3$, and $R^4$ are independently selected from alkyl and aryl groups and $R^5$ and $R^6$ are independently selected from $C_1$–$C_3$ alkyl groups or together form part of a carbocyclic ring containing a —$(CH_2)n$— moiety where n is an integer from 3 to 6;

comprising contacting a 2,2-difluoroketene silyl O,S-acetal of formula (I)

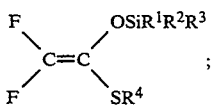

(I)

wherein $R^1$, $R^2$, $R^3$, and $R^4$ are independently selected from alkyl and aryl groups; generated by contacting a difluoro O,S-acetate of the formula

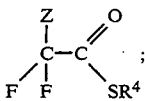

(II)

wherein Z is chloro or hydrogen and $R^4$ is as defined above;
with a halosilane of the formula

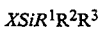 (III)

wherein x is chloro or bromo and $R^1$, $R^2$, and $R^3$ are as defined above;
in a solvent;
provided that when said Z is chloro, the reaction is carried out in the presence of a reducing agent and the contact temperature ranges from about 25° C. to about 80° C.; further provided that when said z is hydrogen, a base is added and the contact temperature ranges from about −78° C. to about 25° C. with a glyceraldehyde derivative of the formula

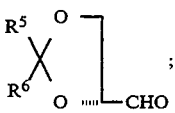

(V)

wherein $R^5$ and $R^6$ are as defined above; at a temperature of about −78° C. to about 80° C.;
provided that a Lewis acid is added when Z is hydrogen.

In yet another aspect, the invention is a 2,2-difluoroketene silyl O,S-acetal of the formula

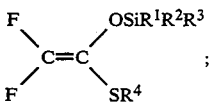

(I)

wherein $R^1$, $R^2$, $R^3$ and $R^4$ are as defined above.

DESCRIPTION OF THE INVENTION

Throughout this document, all temperatures are in degrees Celsius, all proportions, percentages and the like are in weight units and all mixtures are in volume units, except where otherwise indicated. The term "alkyl" alone or in combination refers to straight, cyclic and branched chain aliphatic hydrocarbon groups which contain up to 7 carbon atoms such as, methyl, ethyl, n-propyl, isopropyl, n-butyl, isobutyl, cyclopentyl, cyclohexyl, benzyl, t-butyl, n-pentyl, n-hexyl, 3-methylpentyl groups; and more preferably contain up to 4 carbon atoms. The term "aryl" alone or in combination refers to carbocyclic or heterocyclic groups such as, phenyl, naphthyl, thienyl and substituted derivatives thereof.

The ester of formula (II) suitable for use in the present process such as phenyl chlorodifluorothioacetate and tertbutyl difluorothioactate, are not commercially available. However, they may be prepared, for example, by treating chlorodifluoroacetic anhydride with thiophenol at room temperature and extracting the crude ester product with aqueous sodium bicarbonate. Esters prepared by this procedure include: phenyl-chlorodifluoro thioacetate $^{19}F$ NMR (CDCl$_3$ vs C$_6$F$_6$, ppm) −63.7 (s,CF$_2$Cl); $^1$HNMR (CDCl$_3$,ppm) 7.47 (m, ArH): IR (neat) $\nu_{max}$ 1725 cm$^{-1}$ (CO stretch) and t-butyldifluorothioacetate: b.p. 63° C. @30 mm Hg; $^{19}F$ NMR (C$_6$D$_6$ vs C$_6$F$_6$, ppm) −123.2 (d, J=56 Hz, CF$_2$H); 1HNMR (C$_6$D$_6$, ppm) 5.07 (t, J=56 Hz, CF$_2$H), 1.24 (s, tert-butyl).

The halosilanes of formula (III) suitable for use in the present process are commercially available. An extensive compilation of halosilanes are described in *Petrarch Systems Silanes & Silicones, Register and Review*, Petrarch Systems, 1987. Since halosilanes are commonly employed to introduce silyl protecting groups to organic compounds, they are also discussed by T. W. Greene, et al. in *Protecting Groups in Organic Synthesis*, 2nd Ed., J. Wiley and Sons, Inc. New York (1991). Preferred halosilanes are selected from but not limited to chloro- or bromotrimethylsilyl, triethylsilyl, isopropyldimethylsilyl, t-butyldimethylsilyl, (triphenylmethyl)dimethylsilyl,t-butyldiphenylsilyl, methyldiisopropylsilyl, methyldi-t-butylsilyl, tribenzylsilyl, tri-p-xylysilyl, triisopropylsilyl, and triphenylsilyl.

Solvents suitable for use in the present process are selected from the group consisting of but not limited to tetrahydrofuran, 1,3-dimethyl-2-imidazolidinone, toluene, acetonitrile, glyme, benzene and dichloromethane.

A reducing agent is added to the reaction only when the Z substituent of formula II is chloro. Reducing agents suitable for use in the present process are described by A. Furstner, *Synthesis*, 571 (1989) and include zinc, magnesium, zinc/silver, zinc/silver complexes, cadmium, nickel, indium, cerium, and lithium. Metal salts having a favorable reduction potential may also be used and are selected from chromium(II)chloride, samarium(II)iodide and titanium(II)chloride. Additional reducing agents that are useful include cerium(III)halides, disodium telluride or combinations of trialkylantimonyiodine, tributyl(phenyl) stannyllithium and diethylaluminum chloride. The preferred reducing agent, however, is zinc. The zinc reducing agent may optionally be converted to an activated zinc reducing agent in order to enhance its reactivity. Methods for activating zinc reducing agents are described by Erdik in *Tetrahedron*, 43 (10), 2203-12 (1987).

A base is added to the reaction only when the Z substituent of formula II is hydrogen, as a deprotonating agent. Bases suitable for use in the present process are selected from the group consisting of but not limited to lithium diisopropylamide, lithium hexamethylsilazide, triethylamine, pyridine and n-butyl lithium.

The contact temperature employed to make the compound of formula (I) depends on whether the Z substituent of formula II is chloro or hydrogen. When the Z substituent is chloro, the contact temperature ranges from about 25° C. to about 80° C. However, when the Z substituent is hydrogen, the contact temperature ranges from about −78° C. to about 25° C. Regardless of which z substituent is employed, the reaction is preferably carried out under inert atmospheric conditions and is substantially complete in about 30 minutes to about 24 hours.

It will be recognized by one of ordinary skill in the art that the optimal conditions for preparing the compound of formula (I) under the present process are dramatically influenced by the particular reducing agent employed and its activity. Additional factors that may influence the optimal conditions are the particular halosilane, difluoro ester and solvent employed.

In a subsequent step, the compound of formula (I) may be reacted in situ with a glyceraldehyde derivative of formula (V) to form the α,α-difluoro-β-silyloxy-1,3-dioxolane-4-propanoic acid thioester of formula (IV). Glyceraldehyde derivatives suitable for use in the present process are described by Jurczak, et al. in *Tetrahedron*, 42, 447–488 (1986) and by Schmid and Bradley in *Synthesis*, 587–90 (1992). O-Protected glyceraldehyde derivatives such as 2,3-O-alkylidene glyceraldehydes are particularly useful in the present process; preferred are glyceraldehyde derivatives where the alkylidene protecting group is selected from 2propylidene, 3-pentylidene, cyclopentylidene, or cyclohexylidene protecting groups.

The reaction between the compound of formula (I) and the glyceraldehyde derivative of formula (V) is carried out in situ. As such it constitutes an economical and efficient process for using the inexpensive difluoro O,S-acetate compound of formula (II). The in situ process provides a higher erythro yield of the formula (IV) compound and a significantly higher erythro (anti) selectivity than when the Reformatsky reagent is derived from reacting the compound of formula (II) directly with the compound of formula (V).

The compounds of formula (I) and (V) are contacted in a 1:1 condensation reaction to form the formula (IV) compound. Therefore, in order to achieve maximal conversion of the formula (II) compound, it is important that the formula (V) compound be introduced prior to or at a time when the yield of the formula (I) compound is at a maximum. Since the yield of the formula (IV) compound is based on formula (V), the optimum yield result when the molar equivalents of the formula (V) compound is less than or equal to the molar equivalents of formula (I) formed in situ.

The temperature employed in making the α,α-difluoro-β-silyloxy-1,3-dioxolane-4-propanoic acid thioesters of formula (IV) range from about −78° C. to about 80° C. The reaction is preferably carried out under inert atmospheric conditions and is substantially complete in about 30 minutes to about 24 hours.

The progress of each reaction may be monitored by using $^{19}F$ Nuclear Magnetic Resonance Spectroscopy (NMR).

The compound of formula IV as prepared by the present invention may be isolated by standard isolation techniques employed by organic chemists. However, when boron trifluoride etherate is employed as the Lewis Acid, the silyl protecting group may be cleaved.

The following examples illustrate specific aspects of the present invention and are not intended to limit the scope thereof in any respect and should not be so construed.

Preparation 1

Phenyl chlorodifluorothioacetate

A solution of chlorodifluoroacetic anhydride (10.0 ml) and thiophenol (5.36 ml) in acetonitrile (30 ml) was added to a solution of cobalt(II) chloride (0.5 g) in acetonitrile (100 ml). The mixture was stirred at 25° C. for 36 hours. The acetonitrile was removed in vacuo, and the residue dissolved in diethyl ether (200 ml). The resulting solution was extracted with aqueous sodium bicarbonate and water, dried, and concentrated in vacuo to give 11.23 g of the above product. $^{19}F$ NMR (CDCl$_3$ vs C$_6$F$_6$, ppm) −63.7 (s, CF$_2$Cl); $^1H$ NMR (CDCl$_3$, ppm) 7.47 (m, ArH); IR (neat) $\nu_{max}$ 1725 cm$^{-1}$ (CO stretch).

Example 1

1-Trimethylsiloxy-1-phenylthio-2,2-difluoroethene

Chlorotrimethylsilane (0.68 ml) and phenyl chlorodifluorothioacetate (1.0 g) were added to a slurry of zinc dust (0.32 g) in acetonitrile (10 ml). The mixture was stirred at 40° C. for 3.5 hours then at 25° C. for 18 hours. The mixture was diluted with methyl tert-butyl ether (10 ml), filtered, and concentrated in vacuo to give 1.16 g of the above product as a slightly yellow oil. $^{19}F$ NMR (C$_6$F$_6$ vs C$_6$F$_6$, ppm) −106.0 (d, J=28 Hz), −93.3 (d, J=28 Hz); GC/MS (EI) m/z 261 (M+1)$^+$, 245 (M-15), 183 (M-77), 171 (M-89).

Example 2

1-Trimethylsiloxy-1-phenylthio-2,2-difluoroethene

Chlorotrimethylsilane (1.06 ml) and phenyl chlorodifluorothioacetate (1.55 g) were added to a slurry of zinc dust (0.50 g) in 1,3-dimethyl-2-imidazolidinone (5 ml). The mixture was stirred at 25° C. for 2 hours. The formation of the above product was confirmed by $^{19}F$ NMR spectroscopy. $^{19}F$ NMR (C$_6$F$_6$ vs C$_6$F$_6$, ppm) −106.0 (d, J=28 Hz), −93.3 (d, J=28 Hz).

Example 3

1-Trimethylsiloxy-1-phenylthio-2,2-difluoroethene

Chlorotrimethylsilane (1.06 ml) and phenyl chlorodifluorothioacetate (1.55 g) were added to a slurry of zinc dust (0.50 g) in tetrahydrofuran (10 ml). The mixture was stirred at 50° C. for 2.5 hours. The formation of the above product was confirmed by $^{19}F$ NMR spectroscopy. $^{19}F$ NMR (C$_6$F$_6$ vs C$_6$F$_6$, ppm) −106.0 (d, J=28 Hz), −93.3 (d, J=28 Hz).

Example 4

D-erythro- and D-threo- α,α-difluoro-β-trimethylsilyloxy-2,2-diethyl-1,3-dioxolane-4-propanoic acid, phenylthioester Chlorotrimethylsilane (0.68 ml) and phenyl chlorodifluorothioacetate (1.0 g) were added to a slurry of zinc dust (0.32 g) in 1,3-dimethyl-2-imidazolidinone (10 ml). The mixture was heated to 40° C. for one hour. (R)-2,2-diethyl-1,3-dioxolane-4-carboxaldehyde (0.71 g) was added and the mixture was heated for 18 hours to 80° C. The mixture was then poured into methyl tert-butyl ether (50 ml) and the resulting organic solution washed with water and phosphate buffer. The solution was dried, filtered, and concentrated in vacuo to give 1.79 g of the above product as yellow oil in an erythro and threo isomer ratio (E/T) of 78/22 as determined by Gas Chromatography (GC). $^{19}F$ NMR (CDCl$_3$ vs C$_6$F$_6$, ppm): erythro isomer −111.1 (dd, J$_F$=261 Hz, J$_H$=11 Hz), −115.3 (dd, J$_F$=261 Hz, J$_H$=14 Hz); threo isomer −106.4 (dd, J$_F$=260 Hz, J$_H$=6 Hz), −119.6 (dd, J$_F$=260 Hz, J$_H$=16 Hz); GC/MS (EI) m/z 419 (M+1)$^+$. The stereochemistry was assigned by hydrolysis and cyclization to give known compounds D-2-deoxy-2,2-difluoro-1-oxoribose and D-2-deoxy-2,2-difluoro-1-oxoxylose (Ref. Hertel, et al., *J. Org. Chem.*, 53, 2406 (1988)).

Example 5

D-erythro- and D-threo- α,α-difluoro-β-trimethylsilyloxy-2,2-diethyl-1,3-dioxolane-4-propanoic acid, phenylthioester Chlorotrimethylsilane (0.68 ml) and phenyl chlorodifluorothioacetate (1.0 g) were added to a slurry of zinc dust (0.32 g) in acetonitrile (10 ml). The mixture was heated to 40° C. for three hours. (R)-2,2-diethyl-1,3-dioxolane-4-carboxaldehyde (0.71 g) was added and the mixture heated for 18 hours to 80° C. The mixture was then filtered and the filtrate was poured into methyl tert-butyl ether (50 ml). The resulting organic solution was washed with phosphate buffer, dried, filtered, and concentrated in vacuo to give 1.50 g of the above product as a yellow oil having an E/T ratio of 75/25, determined by GC. $^{19}F$ NMR (CDCl$_3$ vs C$_6$F$_6$, ppm): erythro isomer $-111.1$ (dd, $J_F=261$ Hz, $J_H=11$ Hz), $-115.3$ (dd, $J_F=261$ Hz, $J_H=14$ Hz); threo isomer $-106.4$ (dd, $J_F=260$ Hz, $J_H=6$ Hz), $-119.6$ (dd, $J_F=260$ Hz, $J_H=16$ Hz); GC/MS (EI) m/z 419 (M+1)$^+$. The stereochemistry of the above product was assigned as described in Example 4.

Preparation 2 tert-Butyl difluorothioacetate

Difluoroacetic acid (6.55 ml) was added to a solution of oxalyl chloride (9.08 ml) in acetonitrile (50 ml). The mixture was stirred at 25° C. for 3 hours. tert-butyl thiol (11.74 ml) was added dropwise over 5 minutes. The resulting solution was cooled to 15° C., cobalt (II) chloride (10 mg) was added and the resulting mixture stirred for 17 hours at 25° C. Tert-butyl thiol (4 ml) was added and the solution was stirred for 2 more hours. The solution was dissolved in diethyl ether (500 ml) and extracted with aqueous sodium bicarbonate and water, dried, and concentrated in vacuo to give the above product as a red oil. Vacuum distillation of the oil gave 8.26 of the above product. 19F NMR (C$_6$D$_6$ vs C$_6$F$_6$, ppm) $-123.2$ (d, J=56 Hz, CF$_2$H); 1HNMR (C$_6$D$_6$, ppm) 5.07 (t, J=56 Hz, CF$_2$H), 1.24 (s, tert-butyl).

EXAMPLE 6

1-Trimethylsilyloxy-1-tert-butylthio-2,2-difluoroethene tert-Butyl difluorothioacetate (100 mg) was dissolved in tetrahydrofuran (5 ml) and the solution was cooled to $-78°$ C. Trimethylchlorosilane (151 μl) and lithium diisopropyl amide (327 μl, 2 M solution in heptane/tetrahydrofuran/ethyl-benzene). The solution was stirred for 1 hour at $-78°$ C. then warmed to 25° C. The above product formed in a 65 percent yield as determined by $^{19}F$ NMR Spectroscopy. 19F NMR (C$_6$D$_6$ vs C$_6$F$_6$, ppm) $-104.2$ (d, J=28 Hz), $-92.6$ (d, J=28 Hz).

Example 7

D-erythro and D-threo-α,α-difluoro-β-trimethyl silyloxy-2,2-diethyl-1,3-dioxolane-4-propanoic acid, tert-butyl thioester Chlorotrimethylsilane (0.102 ml) and lithium diisopropyl amide (0.537 ml, 1.5 M solution in cyclohexane) were added to toluene (3 ml) and the solution was cooled to $-78°$ C. tert-Butyl difluorothioacetate (0.113 g) was added dropwise and the solution was stirred for 30 minutes. (R)-2,2-diethyl-1,3-dioxolane-4-carboxaldehyde (0.106 g) and boron trifluoride etherate (0.083 ml) were added and the resulting mixture was stirred at $-78°$ C. for 1.5 hours to obtain the above product.

The above product was then converted to D-erythro and D-threo-α,α-difluoro-β-hydroxy-2,2-diethyl-1,3-dioxolane-4-propanoic acid, tert-butyl thioester as follows. The reaction mixture was quenched with saturated sodium bicarbonate (3 ml) at $-78°$ C. and warmed to 25° C. The mixture was then poured into methyl tertbutyl ether (30 ml) and the resulting organic solution washed with water, dried, filtered and concentrated in vacuo to give 0.160 g of D-erythro and D-threo-α,α-difluoro-β-hydroxy-2,2-diethyl-1,3-dioxolane-4-propanoic acid, tert-butyl thioester as a yellow oil having an erythro/threo isomer ratio of 83/17, determined by GC. $^{19}F$ NMR (C$_6$H$_6$ vs C$_6$F$_6$, ppm): erythro isomer $-113.6$ (dd, $J_F=262$ Hz, $J_H=12$ Hz), $-116.4$ (dd, $J_F=262$ Hz, $J_H=14$ Hz); threo isomer $-107.6$ (dd, $J_F=263$ Hz, $J_H=6$ Hz), $-120.4$ (dd, $J_F=263$ Hz, $J_H=17$ Hz). The stereochemistry of the above product was assigned as described in Example 4.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What I claim is:

1. A process for preparing a 2,2-difluoroketene silyl O,S-acetal of the formula

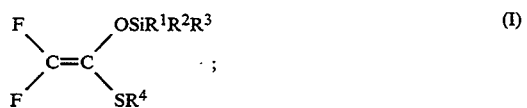

wherein R$^1$, R$^2$, R$^3$, and R$^4$ are independently selected from C$_1$-C$_7$ alkyl, C$_3$-C$_7$ cycloalkyl, phenyl, naphthyl, and thienyl; comprising contacting a difluoro O,S-acetate of the formula

wherein Z is chloro or hydrogen and R$^4$ is as defined above; with a halosilane of the formula

wherein X is chloro or bromo and R$^1$, R$^2$, and R$^3$ are as defined above; in an aprotic solvent; provided that when said Z is chloro, the reaction is carried out in the presence of a reducing agent and the contact temperature ranges from about 25° C. to about 80° C.; further provided that when said Z is hydrogen, a base is added and the contact temperature ranges from about $-78°$ C. to about 25° C.

2. The process of claim 1 wherein the halosilane of formula III is selected from the group consisting of chloro- or bromo- trimethylsilyl, triethylsilyl, isopropyldimethylsilyl, t-butyldimethylsilyl, (triphenylmethyl)dimethylsilyl, t-butyldiphenylsilyl, methyldiisopropylsilyl, methyldi-t-butylsilyl, tribenzylsilyl, tri-p-xylysilyl, triisopropylsilyl, and triphenylsilyl.

3. The process of claim 1 wherein the solvent is selected from the group consisting of tetrahydrofuran, 1,3-dimethyl-2-imidazolidinone, toluene, acetonitrile, glyme, and benzene and dichloromethane.

4. The process of claim 1 wherein the reducing agent is zinc.

5. The process of claim 1 wherein Z is hydrogen, the base is selected from the group consisting of lithium diisopropyl amide, lithium hexamethylsilazide, triethylamine, pyridine and nbutyl lithium.

6. The process of claim 5 wherein the base is lithium diisopropyl amide.

7. The process of claim 1 wherein Z is chloro.

8. A process for preparing $\alpha,\alpha$-difluoro-$\beta$-silyloxy-1,3-dioxolane-4-propanoic acid thioesters of the formula

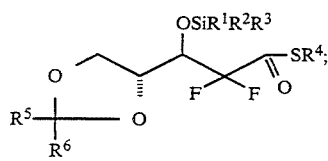 (IV)

wherein $R^1$, $R^2$, $R^3$, and $R^4$ are independently selected from $C_1$–$C_7$ alkyl, $C_3$–$C_7$ cycloalkyl, phenyl naphthyl, and thienyl and $R^5$ and $R^6$ are independently selected from $C_1$–$C_3$ alkyl groups or together form part of a carbocyclic ring containing a —$(CH_2)_n$— moiety where n is an integer from 3 to 6; comprising contacting a 2,2-difluoroketene silyl O,S-acetal of formula (I)

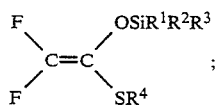 (I)

wherein $R^1$, $R^2$, $R^3$, and $R^4$ are as defined above; generated by contacting a difluoro O,S-acetate of the formula

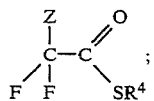 (II)

wherein Z is chloro or hydrogen and $R^4$ is as defined above; with a halosilane of the formula $XSiR^1R^2R^3$ (III);

wherein x is chloro or bromo and $R^1$, $R^2$, and $R^3$ are as defined above; in an aprotic solvent; provided that when said Z is chloro, the reaction is carried out in the presence of a reducing agent and the contact temperature ranges from about 25° C. to about 80° C.; further provided that when said z is hydrogen, a base is added and the contact temperature ranges from about −78° C. to about 25° C.; with a glyceraldehyde derivative of the formula

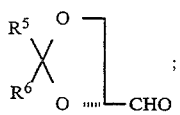 (V)

wherein [$R_5$] $R^5$ and [$R_6$]$R^6$ are as defined above; at a temperature of about −78° C. to about 80° C.; provided that a Lewis acid is added when Z is hydrogen.

9. The process of claim 5 wherein the glyceraldehyde derivative is of the formula

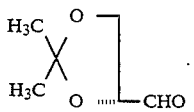 (Va)

10. The process of claim 5 wherein the glyceraldehyde derivative is of the formula

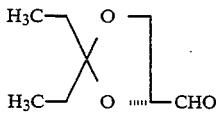 (Vb)

11. A 2,2-difluoroketene silyl [O-S-acetate] O,S-acetate of the formula

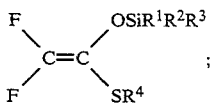 (I)

wherein $R^1$, $R^2$, $R^3$ and $R^4$ are independently selected from $C_1$–$C_7$ alkyl, $C_3$–$C_7$ cycloalkyl, phenyl, naphthyl, and thienyl.

12. The compound of claim 11 wherein $R^4$ is t-butyl.

13. The compound of claim 11 wherein $R^4$ is phenyl.

* * * * *